(12) United States Patent
Griffin et al.

(10) Patent No.: US 7,632,242 B2
(45) Date of Patent: Dec. 15, 2009

(54) CATHETER INCLUDING A COMPLIANT BALLOON

(75) Inventors: Stephen Griffin, San Jose, CA (US); Huey Quoc Chan, San Jose, CA (US); Elaine Lim, Fremont, CA (US); Nhan Hue To, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 729 days.

(21) Appl. No.: 11/008,452

(22) Filed: Dec. 9, 2004

(65) Prior Publication Data

US 2006/0129175 A1    Jun. 15, 2006

(51) Int. Cl.
*A61M 29/00* (2006.01)

(52) U.S. Cl. ............ 604/96.01; 604/93.01; 604/95.03; 604/97.01; 604/102.01; 604/102.02; 604/102.03; 604/103.09; 604/915; 606/192

(58) Field of Classification Search ............ 604/93.01, 604/95.03, 96.01, 97.01, 101.02, 102.01, 604/102.02, 102.03, 103.03, 103.08, 103.09, 604/915; 606/108, 192

See application file for complete search history.

(56) References Cited

U.S. PATENT DOCUMENTS

| | | | |
|---|---|---|---|
| 2,441,166 A | 5/1948 | Raspert | |
| 3,452,742 A | 7/1969 | Muller | |
| 3,625,200 A | 12/1971 | Muller | |
| 3,890,977 A | 6/1975 | Wilson | |
| 4,003,369 A | 1/1977 | Heilman et al. | |
| 4,020,829 A | 5/1977 | Willson et al. | |
| 4,215,703 A | 8/1980 | Wilson | |
| 4,327,736 A | 5/1982 | Inoue | |
| 4,425,919 A | 1/1984 | Alston, Jr. et al. | |
| 4,545,390 A | 10/1985 | Leary | |
| 4,547,193 A | 10/1985 | Rydell | |
| 4,563,181 A | 1/1986 | Wijayarathna et al. | |
| 4,637,396 A * | 1/1987 | Cook ..................... 606/194 |
| 4,665,906 A | 5/1987 | Jervis | |
| 4,690,672 A | 9/1987 | Veltrup | |
| 4,717,379 A | 1/1988 | Ekholmer | |
| 4,721,117 A | 1/1988 | Mar et al. | |
| 4,763,647 A | 8/1988 | Gambale | |
| 4,781,186 A | 11/1988 | Simpson et al. | |
| 4,796,629 A | 1/1989 | Grayzel | |
| 4,800,890 A | 1/1989 | Cramer | |

(Continued)

FOREIGN PATENT DOCUMENTS

AU    723040    12/1997

(Continued)

OTHER PUBLICATIONS

"Mechanical Design and Systems Handbook", H.A. Rothbart, 1964, p. 33-13 (one sheet).

*Primary Examiner*—Nicholas D Lucchesi
*Assistant Examiner*—Quynh-Nhu H Vu
(74) *Attorney, Agent, or Firm*—Crompton, Seager & Tufte, LLC

(57) ABSTRACT

A catheter having an elongate shaft including a plurality of apertures disposed along at least a length of the shaft to facilitate bending. The catheter includes an inflatable balloon, wherein a subset of the plurality of apertures provides fluid communication from an inflation lumen to the inflatable balloon.

29 Claims, 6 Drawing Sheets

U.S. PATENT DOCUMENTS

| | | | |
|---|---|---|---|
| 4,811,743 A | 3/1989 | Stevens | |
| 4,827,941 A | 5/1989 | Taylor et al. | |
| 4,832,047 A | 5/1989 | Sepetka et al. | |
| 4,846,186 A | 7/1989 | Box et al. | |
| 4,846,193 A | 7/1989 | Tremulis et al. | |
| 4,867,173 A | 9/1989 | Leoni | |
| 4,875,489 A | 10/1989 | Messner et al. | |
| 4,884,579 A | 12/1989 | Engelson | |
| 4,911,148 A | 3/1990 | Sosnowski et al. | |
| 4,917,102 A | 4/1990 | Miller et al. | |
| 4,921,476 A | 5/1990 | Wuchinich | |
| 4,932,959 A | 6/1990 | Horzewski et al. | |
| 4,934,380 A | 6/1990 | Toledo | |
| 4,953,553 A | 9/1990 | Tremulis | |
| 4,955,384 A | 9/1990 | Taylor et al. | |
| 4,955,862 A | 9/1990 | Sepetka | |
| 4,964,409 A | 10/1990 | Tremulis | |
| 4,966,163 A | 10/1990 | Kraus et al. | |
| 4,989,608 A | 2/1991 | Ratner | |
| 4,994,033 A | 2/1991 | Shockey et al. | |
| 4,994,069 A | 2/1991 | Ritchart et al. | |
| 4,998,923 A * | 3/1991 | Samson et al. | 606/194 |
| 5,007,434 A | 4/1991 | Doyle et al. | |
| 5,011,488 A | 4/1991 | Ginsburg | |
| 5,040,543 A | 8/1991 | Badera et al. | |
| 5,049,132 A | 9/1991 | Shaffer et al. | |
| 5,052,404 A | 10/1991 | Hodgson | |
| 5,063,935 A | 11/1991 | Gamble | |
| 5,037,609 A | 12/1991 | Summers et al. | |
| 5,084,013 A | 1/1992 | Takase | |
| 5,087,244 A | 2/1992 | Wolinsky et al. | |
| 5,095,915 A | 3/1992 | Engelson | |
| 5,106,455 A | 4/1992 | Jacobsen et al. | |
| 5,125,395 A | 6/1992 | Adair | |
| 5,141,518 A | 8/1992 | Hess et al. | |
| 5,144,959 A | 9/1992 | Gambale et al. | |
| 5,147,317 A | 9/1992 | Shank et al. | |
| 5,181,668 A | 1/1993 | Tsuji et al. | |
| 5,205,830 A | 4/1993 | Dassa et al. | |
| 5,211,183 A | 5/1993 | Wilson | |
| 5,213,576 A | 5/1993 | Abiuso et al. | |
| 5,228,441 A | 7/1993 | Lundquist | |
| 5,232,444 A | 8/1993 | Just et al. | |
| 5,238,004 A | 8/1993 | Sahatjian et al. | |
| 5,242,759 A | 9/1993 | Hall | |
| 5,243,996 A | 9/1993 | Hall | |
| 5,250,069 A | 10/1993 | Nobuyoshi et al. | |
| 5,254,106 A | 10/1993 | Feaster | |
| 5,254,107 A | 10/1993 | Soltesz | |
| 5,256,143 A * | 10/1993 | Miller et al. | 604/102.02 |
| 5,256,144 A * | 10/1993 | Kraus et al. | 604/96.01 |
| 5,259,393 A | 11/1993 | Corso, Jr. et al. | |
| 5,267,979 A | 12/1993 | Appling et al. | |
| 5,300,032 A | 4/1994 | Hibbs et al. | |
| 5,304,131 A | 4/1994 | Paskar | |
| 5,306,252 A | 4/1994 | Yutori et al. | |
| 5,315,996 A | 5/1994 | Lundquist | |
| 5,318,518 A | 6/1994 | Plechinger et al. | |
| 5,322,064 A | 6/1994 | Lundquist | |
| 5,329,923 A | 7/1994 | Lundquist | |
| 5,330,429 A | 7/1994 | Noguchi et al. | |
| 5,333,620 A | 8/1994 | Moutafis et al. | |
| 5,334,145 A | 8/1994 | Lundquist et al. | |
| 5,336,205 A | 8/1994 | Zenzen et al. | |
| 5,341,818 A | 8/1994 | Abrams et al. | |
| 5,345,937 A | 9/1994 | Middleman et al. | |
| 5,345,945 A | 9/1994 | Hodgson et al. | |
| 5,365,942 A | 11/1994 | Shank | |
| 5,365,943 A | 11/1994 | Jansen | |
| 5,368,564 A | 11/1994 | Savage | |
| 5,370,609 A | 12/1994 | Drasler et al. | |
| 5,376,084 A | 12/1994 | Bacich et al. | |
| 5,406,960 A | 4/1995 | Corso, Jr. | |
| 5,411,476 A | 5/1995 | Abrams | |
| 5,437,288 A | 8/1995 | Schwartz et al. | |
| 5,438,993 A | 8/1995 | Lynch et al. | |
| 5,439,000 A | 8/1995 | Gunderson et al. | |
| 5,441,483 A | 8/1995 | Avitall | |
| 5,441,489 A | 8/1995 | Utsumi et al. | |
| 5,460,187 A | 10/1995 | Daigle et al. | |
| 5,477,856 A | 12/1995 | Lundquist | |
| 5,507,301 A | 4/1996 | Wasicek et al. | |
| 5,507,729 A | 4/1996 | Lindenberg et al. | |
| 5,507,751 A | 4/1996 | Goode et al. | |
| 5,507,766 A | 4/1996 | Kugo et al. | |
| 5,514,128 A | 5/1996 | Hillsman et al. | |
| 5,520,194 A | 5/1996 | Miyata et al. | |
| 5,520,645 A | 5/1996 | Imran et al. | |
| 5,527,292 A | 6/1996 | Adams et al. | |
| 5,538,504 A | 7/1996 | Linden et al. | |
| 5,538,512 A * | 7/1996 | Zenzon et al. | 604/508 |
| 5,551,444 A | 9/1996 | Finlayson | |
| 5,554,119 A | 9/1996 | Harrison et al. | |
| 5,554,139 A | 9/1996 | Okajima | |
| 5,558,642 A | 9/1996 | Schweich, Jr. et al. | |
| 5,562,619 A | 10/1996 | Mirarchi et al. | |
| 5,569,197 A | 10/1996 | Helmus et al. | |
| 5,569,218 A | 10/1996 | Berg | |
| 5,571,073 A | 11/1996 | Castillo | |
| 5,573,520 A * | 11/1996 | Schwartz et al. | 604/526 |
| 5,584,821 A | 12/1996 | Hobbs et al. | |
| 5,599,492 A | 2/1997 | Engelson | |
| 5,601,539 A | 2/1997 | Corso, Jr. | |
| 5,605,162 A | 2/1997 | Mirzaee et al. | |
| 5,611,775 A | 3/1997 | Machold et al. | |
| 5,622,184 A | 4/1997 | Ashby et al. | |
| 5,637,089 A | 6/1997 | Abrams et al. | |
| 5,666,968 A | 9/1997 | Imran et al. | |
| 5,666,969 A | 9/1997 | Urick et al. | |
| 5,676,659 A | 10/1997 | McGurk | |
| 5,682,894 A | 11/1997 | Orr et al. | |
| 5,688,234 A | 11/1997 | Frisbie | |
| 5,690,120 A | 11/1997 | Jacobsen et al. | |
| 5,720,300 A | 2/1998 | Fagan et al. | |
| 5,722,609 A | 3/1998 | Murakami | |
| 5,728,063 A | 3/1998 | Preissman et al. | |
| 5,741,429 A | 4/1998 | Donadio, III et al. | |
| 5,746,701 A | 5/1998 | Noone | |
| 5,749,858 A | 5/1998 | Cramer | |
| 5,766,201 A | 6/1998 | Ravenscroft et al. | |
| 5,769,830 A | 6/1998 | Parker | |
| 5,772,609 A | 6/1998 | Nguyen et al. | |
| 5,788,654 A | 8/1998 | Schwager | |
| 5,792,124 A | 8/1998 | Horrigan et al. | |
| 5,795,331 A | 8/1998 | Cragg et al. | |
| 5,797,856 A | 8/1998 | Frisbie et al. | |
| 5,800,454 A | 9/1998 | Jacobsen et al. | |
| 5,807,249 A | 9/1998 | Qin et al. | |
| 5,827,225 A | 10/1998 | Ma Schwab | |
| 5,827,229 A | 10/1998 | Auth et al. | |
| 5,827,242 A | 10/1998 | Follmer et al. | |
| 5,827,424 A | 10/1998 | Follmer et al. | |
| 5,833,632 A | 11/1998 | Jacobsen et al. | |
| 5,833,650 A | 11/1998 | Imran | |
| 5,833,658 A | 11/1998 | Levy et al. | |
| 5,836,926 A | 11/1998 | Peterson et al. | |
| 5,843,033 A | 12/1998 | Ropiak | |
| 5,843,050 A | 12/1998 | Jones et al. | |
| 5,843,051 A | 12/1998 | Adams et al. | |
| 5,843,244 A | 12/1998 | Pelton et al. | |
| 5,851,203 A | 12/1998 | van Muiden | |
| 5,866,561 A | 2/1999 | Ungs | |
| 5,879,361 A | 3/1999 | Nash | |
| 5,891,111 A | 4/1999 | Ismael | |

| | | |
|---|---|---|
| 5,897,537 A | 4/1999 | Berg et al. |
| 5,902,254 A | 5/1999 | Magram |
| 5,904,657 A | 5/1999 | Unsworth et al. |
| 5,906,618 A | 5/1999 | Larson, III |
| 5,911,715 A | 6/1999 | Berg et al. |
| 5,911,717 A | 6/1999 | Jacobsen et al. |
| 5,916,178 A | 6/1999 | Noone |
| 5,916,192 A | 6/1999 | Nita et al. |
| 5,916,194 A | 6/1999 | Jacobsen et al. |
| 5,919,163 A | 7/1999 | Glickman |
| 5,931,830 A | 8/1999 | Jacobsen et al. |
| 5,935,108 A | 8/1999 | Katoh et al. |
| 5,947,985 A | 9/1999 | Imran |
| 5,951,458 A | 9/1999 | Hastings et al. |
| 5,971,975 A | 10/1999 | Mills et al. |
| 5,980,532 A | 11/1999 | Wang |
| 5,989,271 A | 11/1999 | Bonnette et al. |
| 6,001,068 A | 12/1999 | Uchino et al. |
| 6,004,279 A | 12/1999 | Crowley et al. |
| 6,014,919 A | 1/2000 | Jacobsen et al. |
| 6,017,319 A | 1/2000 | Jacobsen et al. |
| 6,022,336 A | 2/2000 | Zadno-Azizi et al. |
| 6,022,369 A | 2/2000 | Jacobsen et al. |
| 6,045,547 A | 4/2000 | Ren et al. |
| 6,048,339 A | 4/2000 | Zirps et al. |
| 6,059,809 A | 5/2000 | Amor et al. |
| 6,063,101 A | 5/2000 | Jacobsen et al. |
| 6,063,200 A | 5/2000 | Jacobsen et al. |
| 6,066,361 A | 5/2000 | Jacobsen et al. |
| 6,102,929 A | 8/2000 | Conway et al. |
| 6,106,485 A | 8/2000 | McMahon |
| 6,106,488 A | 8/2000 | Fleming et al. |
| 6,120,477 A | 9/2000 | Campbell et al. |
| 6,120,523 A | 9/2000 | Crocker et al. |
| 6,139,510 A | 10/2000 | Palermo |
| 6,149,641 A | 11/2000 | Ungs et al. |
| 6,165,292 A | 12/2000 | Abrams et al. |
| 6,171,296 B1 | 1/2001 | Chow |
| 6,183,410 B1 | 2/2001 | Jacobsen et al. |
| 6,186,978 B1 * | 2/2001 | Samson et al. ............ 604/96.01 |
| 6,214,042 B1 | 4/2001 | Jacobsen et al. |
| 6,217,567 B1 | 4/2001 | Zadno-Azizi et al. |
| 6,231,543 B1 | 5/2001 | Hegde et al. |
| 6,231,588 B1 | 5/2001 | Zadno-Azizi |
| 6,234,995 B1 | 5/2001 | Peacock, III |
| 6,251,092 B1 | 6/2001 | Qin et al. |
| 6,260,458 B1 | 7/2001 | Jacobsen et al. |
| 6,280,411 B1 | 8/2001 | Lennox |
| 6,287,320 B1 | 9/2001 | Slepian |
| 6,290,656 B1 | 9/2001 | Boyle et al. |
| 6,296,616 B1 | 10/2001 | McMahon |
| 6,296,631 B2 | 10/2001 | Chow |
| 6,302,870 B1 | 10/2001 | Jacobsen et al. |
| 6,315,757 B1 * | 11/2001 | Chee et al. ............. 604/103.09 |
| 6,325,790 B1 | 12/2001 | Trotta |
| 6,338,725 B1 | 1/2002 | Hermann et al. |
| 6,346,091 B1 | 2/2002 | Jacobsen et al. |
| 6,352,515 B1 | 3/2002 | Anderson et al. |
| 6,355,027 B1 | 3/2002 | Le et al. |
| 6,368,315 B1 | 4/2002 | Gillis et al. |
| 6,368,316 B1 | 4/2002 | Jansen et al. |
| 6,379,369 B1 | 4/2002 | Abrams et al. |
| 6,390,993 B1 | 5/2002 | Cornish et al. |
| 6,398,758 B1 | 6/2002 | Jacobsen et al. |
| 6,428,489 B1 | 8/2002 | Jacobsen et al. |
| 6,431,039 B1 | 8/2002 | Jacobsen et al. |
| 6,440,088 B1 | 8/2002 | Jacobsen et al. |
| 6,478,778 B1 | 11/2002 | Jacobsen et al. |
| 6,491,648 B1 * | 12/2002 | Cornish et al. ............. 600/585 |
| 6,491,671 B1 | 12/2002 | Larson, III et al. |
| 6,508,803 B1 | 1/2003 | Horikawa et al. |
| 6,511,503 B1 | 1/2003 | Burkett et al. |
| 6,524,301 B1 | 2/2003 | Wilson et al. |
| 6,530,934 B1 | 3/2003 | Jacobsen et al. |
| 6,553,880 B2 | 4/2003 | Jacobsen et al. |
| 6,579,246 B2 | 6/2003 | Jacobsen et al. |
| 6,602,280 B2 | 8/2003 | Chobotov |
| 6,610,046 B1 | 8/2003 | Usami et al. |
| 6,623,452 B2 | 9/2003 | Chien et al. |
| 6,638,245 B2 | 10/2003 | Miller et al. |
| 6,648,854 B1 | 11/2003 | Patterson et al. |
| 6,652,508 B2 | 11/2003 | Griffin et al. |
| 6,776,720 B2 | 7/2004 | Jacobsen et al. |
| 2002/0013540 A1 | 1/2002 | Jacobsen et al. |
| 2002/0019599 A1 | 2/2002 | Rooney et al. |
| 2002/0077594 A1 | 6/2002 | Chien et al. |
| 2002/0082499 A1 | 6/2002 | Jacobsen et al. |
| 2003/0009208 A1 | 1/2003 | Snyder et al. |
| 2003/0060732 A1 | 3/2003 | Jacobsen et al. |
| 2003/0069520 A1 | 4/2003 | Skujins et al. |
| 2003/0069521 A1 | 4/2003 | Reynolds et al. |
| 2003/0069522 A1 | 4/2003 | Jacobsen et al. |
| 2003/0093059 A1 | 5/2003 | Griffin et al. |
| 2003/0105415 A1 | 6/2003 | Mirigian |
| 2003/0125709 A1 | 7/2003 | Eidenschink |
| 2003/0130672 A1 | 7/2003 | DoBrava et al. |
| 2004/0002713 A1 | 1/2004 | Olson, Jr. et al. |
| 2004/0111044 A1 | 6/2004 | Davis et al. |
| 2004/0181174 A2 | 9/2004 | Davis et al. |

FOREIGN PATENT DOCUMENTS

| | | |
|---|---|---|
| AU | 733966 | 4/1998 |
| BR | PI 9712829-5 | 1/2000 |
| CN | 1230914 A | 10/1999 |
| DE | 25 39 191 A | 3/1976 |
| EP | 0 521 595 A2 | 1/1993 |
| EP | 0 608 853 A2 | 8/1994 |
| EP | 0 778 038 A2 | 6/1997 |
| EP | 0 778 039 A1 | 6/1997 |
| EP | 0 778 040 A2 | 6/1997 |
| EP | 0 790 066 A3 | 8/1997 |
| EP | 0 812 599 B1 | 12/1997 |
| EP | 0 835 673 A2 | 4/1998 |
| EP | 0 865 773 A1 | 9/1998 |
| EP | 0 917 885 A1 | 5/1999 |
| EP | 0 935 947 B1 | 8/1999 |
| EP | 0 937 481 A1 | 8/1999 |
| JP | 63-181774 A | 7/1988 |
| JP | 5-507857 A | 11/1993 |
| JP | 6-501179 A | 2/1994 |
| JP | 7-28562 U | 1/1995 |
| JP | 7-51067 Y2 | 2/1995 |
| JP | 9-276413 A | 10/1997 |
| JP | 9-294813 A | 11/1997 |
| JP | 10-305039 | 11/1998 |
| JP | 10-328191 A | 12/1998 |
| JP | 11-226131 A | 8/1999 |
| JP | 11-267224 A | 10/1999 |
| JP | 11-276491 A | 10/1999 |
| JP | 2000-510722 A | 8/2000 |
| JP | 2000-511083 A | 8/2000 |
| JP | 2001-500808 A | 1/2001 |
| JP | 2002-529137 A | 9/2002 |
| JP | 2002-542901 A | 12/2002 |
| JP | 2002-543896 A | 12/2002 |
| JP | 2003-517893 A | 6/2003 |
| WO | WO 92/07619 A1 | 5/1992 |
| WO | WO 93/04722 A2 | 3/1993 |
| WO | WO 95/24236 A1 | 9/1995 |
| WO | WO 96/19255 A1 | 6/1996 |
| WO | WO 97/43949 A1 | 11/1997 |
| WO | WO 97/44083 A1 | 11/1997 |
| WO | WO 97/44086 A1 | 11/1997 |
| WO | WO 98/10694 A2 | 3/1998 |
| WO | WO 98/39047 A1 | 9/1998 |

| | | | | | | |
|---|---|---|---|---|---|---|
| WO | WO 99/11313 | A1 | 3/1999 | WO | WO 00/72907 A1 | 12/2000 |
| WO | WO 00/27303 | A2 | 5/2000 | WO | WO 01/28620 A1 | 4/2001 |
| WO | WO 00/30710 | A1 | 6/2000 | WO | WO 01/45773 A1 | 6/2001 |
| WO | WO 00/48645 | A2 | 8/2000 | WO | WO 01/93920 A2 | 12/2001 |
| WO | WO 00/57943 | A1 | 10/2000 | WO | WO 02/13682 A1 | 2/2002 |
| WO | WO 00/66199 | A1 | 11/2000 | WO | WO 03/004086 A2 | 1/2003 |
| WO | WO 00/67845 | A1 | 11/2000 | | | |
| WO | WO 00/69323 | A2 | 11/2000 | | | |

* cited by examiner

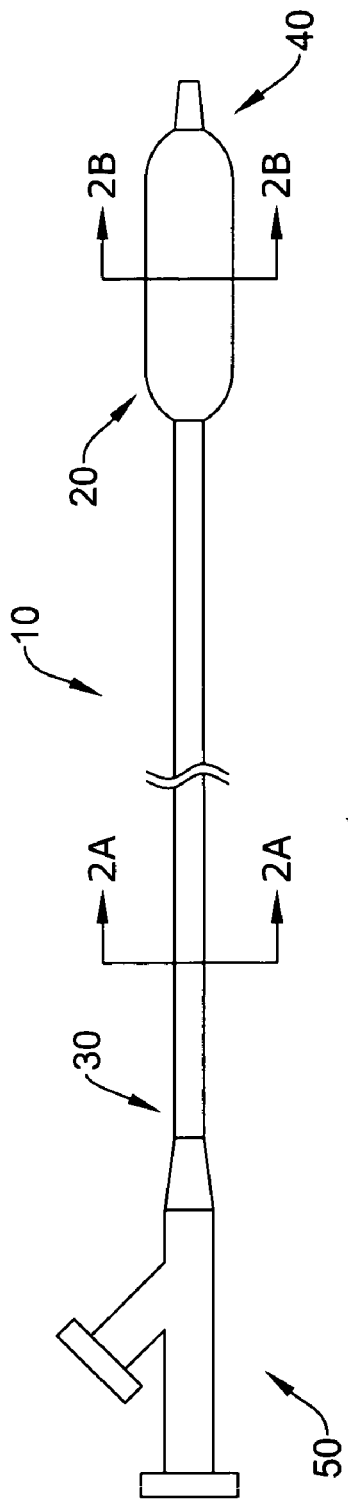
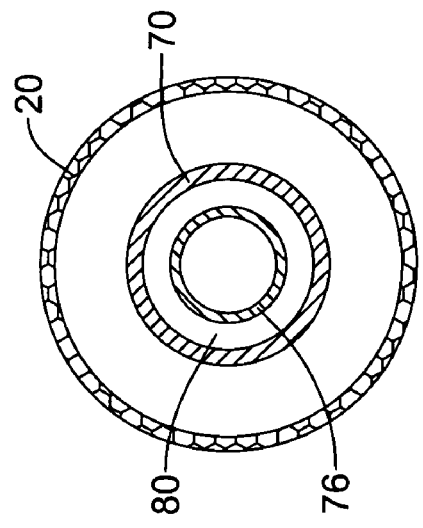
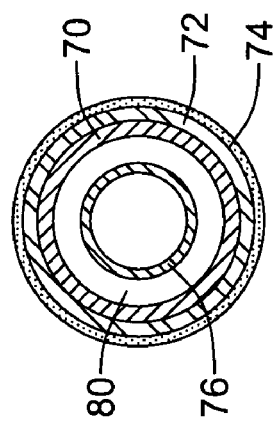

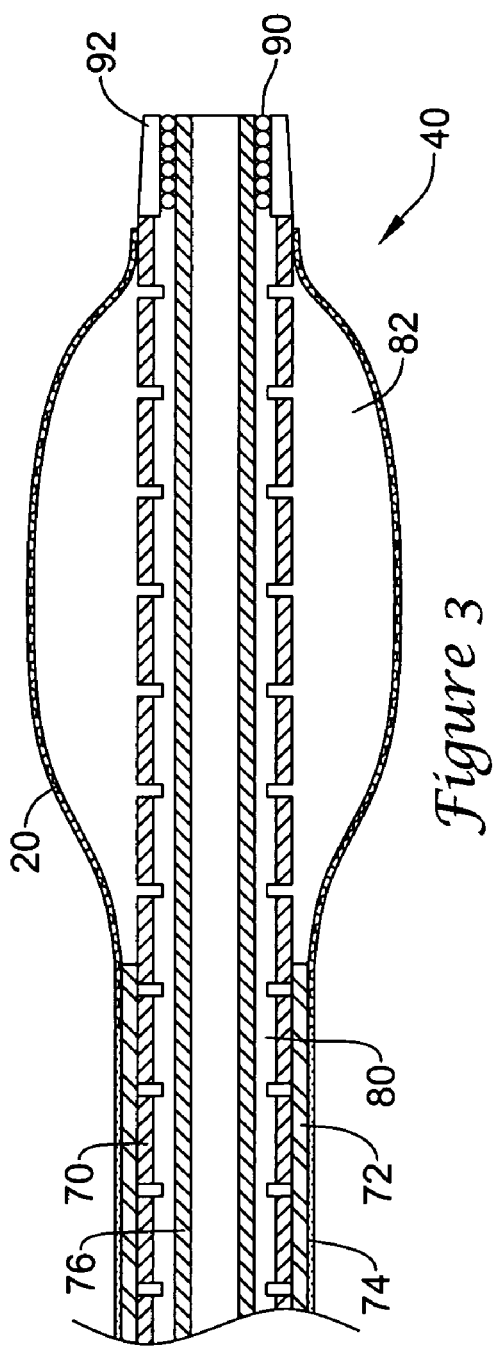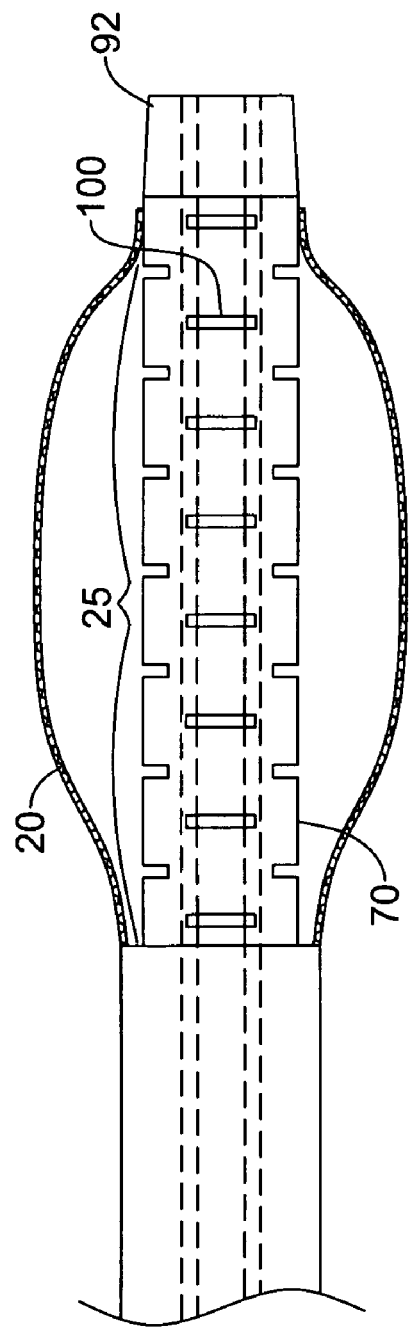

CATHETER INCLUDING A COMPLIANT BALLOON

FIELD OF THE INVENTION

The present invention generally relates to medical devices for navigating body lumens. More specifically, the present invention relates to flexible medical devices for providing an inflatable balloon in a body lumen during a medical procedure.

BACKGROUND OF THE INVENTION

Medical devices such as intravascular and endovascular catheters are commonly used in medical procedures such as treatment of aneurysms, arteriovenous malformations (AVM), arteriovenous fistulae (AVF), as well as, intracranial procedures, neurological procedures, radiological procedures, and peripheral vascular procedures. There is an ongoing need to develop medical devices possessing improved characteristics in order to facilitate navigation of the tortuous vasculature of the human body during a medical procedure.

SUMMARY OF THE INVENTION

The present invention provides a medical device having improved characteristics for use during a medical procedure. The present invention includes an elongate shaft having a plurality of apertures formed along the length of the shaft to increase and/or control catheter flexibility and facilitate bending. An inflatable balloon may be placed at a distal portion of the elongate shaft and a hub assembly may be placed at a proximal portion of the elongate shaft. The hub assembly may include an inflation port in fluid communication with the inflatable balloon. There may be a polymer layer disposed along the portion of the shaft between the hub assembly and the inflatable balloon. The polymer layer covers the apertures along this portion to provide a fluid tight seal within the elongate shaft, while any apertures located on the portion of the elongate shaft including the hub assembly and the inflatable balloon remain unobstructed. Therefore, an inflation passageway is formed from the hub assembly, through the lumen of the elongate shaft, through the unobstructed apertures to the inflatable balloon.

BRIEF DESCRIPTION OF THE DRAWINGS

The invention may be more completely understood in consideration of the following detailed description of various embodiments of the invention in connection with the accompanying drawings, in which:

FIG. 1 is a plan view of a balloon catheter in accordance with an embodiment of the invention;

FIG. 2A is a cross-section taken along line 2A-2A in FIG. 1;

FIG. 2B is a cross-section taken along line 2B-2B in FIG. 1;

FIG. 3 is a cross-sectional view of the distal portion of a balloon catheter in accordance with an embodiment of the invention;

FIG. 4 is a partially sectioned view of the distal portion of a balloon catheter as embodied in FIG. 3;

DETAILED DESCRIPTION OF PREFERRED EMBODIMENTS

Figure 6:
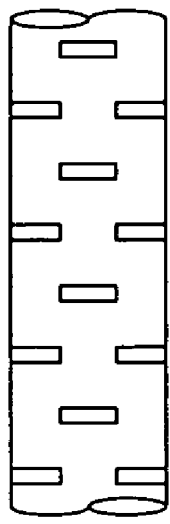
FIGS. 5-8 are alternate embodiments of a portion of the catheter in accordance with the invention.
Figure 8:
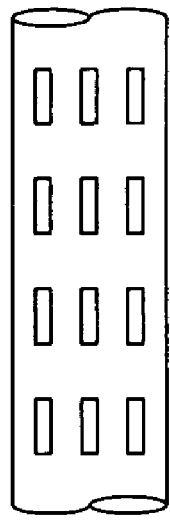
Figure 5:
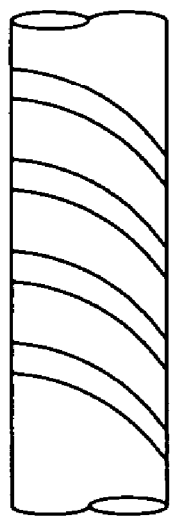
Figure 7:
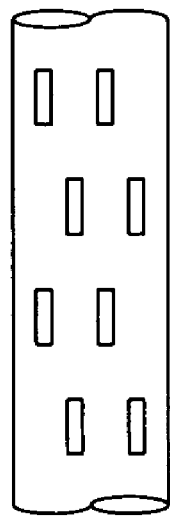

The following detailed description should be read with reference to the drawings in which similar elements in different drawings are numbered the same. The detailed description and the drawings, which are not necessarily to scale, depict illustrative embodiments and are not intended to limit the scope of the invention.

FIG. 1 generally shows a catheter 10 within the scope of the invention. In a preferred embodiment, the catheter 10 can include a distal portion 40 including an inflatable balloon 20 and a proximal portion 30 including a hub assembly 50. The catheter 10 can also include an elongate shaft 15 extending from the proximal portion 30 to the distal portion 40. The catheter 10 may have a length that is in the range of about 50 centimeters to about 250 centimeters.

FIG. 2A shows a cross-section of catheter 10 taken along line 2A-2A. As shown in FIG. 2A, the elongate shaft 10 may include an outer tubular member 70. The outer tubular member 70 may be formed of materials such as metals, metal alloys, polymers, metal-polymer composites, or other suitable materials. Some examples of some suitable materials may include stainless steels (e.g., 304v stainless steel), nickel-titanium alloys (e.g., nitinol, such as super elastic or linear elastic nitinol), nickel-chromium alloys, nickel-chromium-iron alloys, cobalt alloys, nickel, titanium, platinum, or alternatively, a polymer material such as a high performance polymer, or other suitable materials, and the like.

As can be better shown in FIGS. 5-8, outer tubular member 70 may include a plurality of apertures 100 formed along the length of outer tubular member 70 to increase the flexibility of the elongate shaft 15 to a desired level. Apertures 100 may be slots, slits, grooves, helical cuts, or the like. The spacing, depth and type of apertures 100 may be varied to control the flexure profile and torsional stiffness of the outer tubular member 70. The spacing of apertures 100 may vary gradually along outer tubular member 70, or may change incrementally. Apertures 100 may extend through the wall of the outer tubular member 70, or they may extend only partially through the wall. It is contemplated that at least some of the apertures extend through the wall of the outer tubular member 70. Apertures may be micromachined into the outer tubular member 70 by electrostatic discharge machining (EDM), chemical milling, ablation, laser cutting, saw cutting, grinding, etching, or the like. Apertures 100 may extend substantially the full length of the elongate shaft 15, or apertures may be positioned along selected portions of the elongate shaft 15 where increased flexibility is desired. Such techniques for creating apertures 100 along the outer tubular member 70 are discussed in detail in U.S. Patent Publication 2003/0069522 to Jacobsen et al., as herein incorporated by reference in its entirety.

A polymer layer 72 may be disposed about at least a portion of the outer tubular member 70. Polymer layer 72 may extend from the proximal portion 30 to the distal portion 40 of outer tubular member 70. The polymer layer may cover the apertures 100 along a portion of the outer tubular member 70, providing the outer tubular member 70 with a fluid tight seal along the portion having the polymer 72. Polymer layer 72 may be formed of a flexible material such as polyurethane, low-density polyethylene (LDPE), polyvinyl chloride, polyether block amide (PEBAX), styrene-ethylene/butylenes-styrene (SEBS), styrene-butadiene-styrene (SBS), as well as other polymers of suitable properties.

In some embodiments, part of or all of the elongate shaft 15 may be coated with a lubricious layer 74 such as a hydrophilic polymer such as polyarylene oxides, polyvinylpyrolidones, polyvinylalcohols, hydroxyl alkyl cellulosics, aligns, saccharides, caprolactones, and the like, and mixtures and combinations thereof. Lubricious layer 74 may improve steerability and improve lesion crossing capability of the catheter 10. The lubricious layer 74 may be chemically bonded to polymer layer 72 or physically coated on the surface of polymer layer 72. In some embodiments, a distal portion of the catheter 10 may be coated with a hydrophilic polymer, while the more proximal portions may be coated with a fluoropolymer. Lubricious layer 74 may be absent from the elongate shaft, or a portion thereof.

As shown in FIG. 2A, an inner tubular member 76 may be disposed within the outer tubular member 70. The outer surface of the inner tubular member 76 is spaced away from the inner surface of the outer tubular member 70, defining an annular inflation lumen 80 therebetween. The inner tubular member 76 may extend substantially the entire length of the catheter 10. The inner tubular member may provide a lumen 78 for a guidewire or delivering a medical device.

The inner tubular member 76 may be formed of materials such as metals, metal alloys, polymers, metal-polymer composites, or other suitable materials. Some examples of some suitable materials may include high-density polyethylene (HDPE), low-density polyethylene (LDPE), silicon, fluoropolymer, liquid crystal polymer (LCP), polyimide, polyamide, polyester, polyethylene (PE), polypropylene, polyvinyl chloride (PVC), polyfluorocarbon, polyurethane, polysulfone, ethyl vinyl acetate (EVA), polyether block amide (PEBAX), styrene-ethylene/butylenes-styrene (SEBS), styrene-butadiene-styrene (SBS), polyethylene terephthalate (PET), and their mixtures, alloys, blends, copolymers, and block copolymers.

FIG. 2B shows a cross-section taken along line 2B-2B at distal portion 40 of catheter 10. Distal portion 40 includes inflatable balloon 20 disposed about elongate shaft 15. In one embodiment, the inflatable balloon 20 is a compliant inflatable membrane with elastomeric properties. Inflatable balloon 20 may be formed of a urethane polymer or a thermoplastic rubber elastomer, such as Chronoprene™, available from CardioTech International, Inc. The balloon 20 may be expandable between a collapsed configuration and an inflated configuration. Upon inflation, the balloon 20 may conform to the shape of the interior of a body lumen in which the catheter 10 is disposed, such as a blood vessel. In the collapsed configuration (not shown), the balloon 20 may be collapsed about the distal portion 20 of the catheter 10 to create a low profile. As can be seen in FIG. 2B, at least a portion of the outer tubular member 70 of the elongate shaft 15 proximate the inflatable balloon 20 is free of the polymer layer 72. As can more clearly be seen in FIG. 4, apertures 100 along the portion of the outer tubular member 70 including the balloon 20 are free of the polymer layer 72. Unobstructed apertures 100 may be a subset of the apertures 100 extending along the length of the outer tubular member 70. Unobstructed apertures 100 along distal balloon section 25 are preferably formed during the same process as forming apertures 100 along the length of the outer tubular member 70, as discussed above. Unobstructed apertures 100 in distal balloon section 25 allow for fluid communication between the interior of the balloon 82 and inflation lumen 80. Inflation of the balloon 20 will be described in more detail with regard to FIGS. 3 and 4.

FIGS. 3 and 4 show a distal portion 40 of the catheter 10. FIG. 3 shows a cross-sectional view of the distal portion 40, while FIG. 4 shows a plan view of distal portion 40 with inflatable balloon 20 shown in cross-section. The distal portion 40 of the catheter 10 includes a distal balloon section 25 free of the polymer layer 72. The distal balloon section 25 may extend substantially the length of the balloon 20 or a portion thereof. The distal balloon section 25 includes a subset of apertures 100 formed about outer tubular member 70. At least some of apertures 100 in distal balloon section 25 extend through the wall of outer tubular member 70. Unobstructed apertures 100 in the distal balloon section 25 provide fluid communication between the interior of the balloon 82 and inflation lumen 80. Further, it is noted that flexibility under the balloon can be dramatically increased by the combination of multiple apertures and lack of polymer coating, which would tend to reduce flexibility. Further, the multiple apertures allow for quick inflation/deflation of the balloon.

A distal tip 92 may be placed distal of the balloon 20. Inner tubular member 76 may extend into distal tip 92. Distal tip may include a coil 90 to provide flexibility during navigation of the tortuous vasculature. Distal tip 92 may occlude the distal end of inflation lumen 80 to provide a fluid-tight passageway along the length of elongate shaft 15 to inflatable balloon 20. Distal tip may include radiopaque material. Radiopaque materials are understood to be materials capable of producing a relatively bright image on a fluoroscopy screen or other imaging technique during a medical procedure. Some examples of radiopaque materials may include, but are not limited to, gold, platinum, palladium, tantalum, tungsten alloy, plastic material loaded with a radiopaque filler, and the like.

Figure 9:
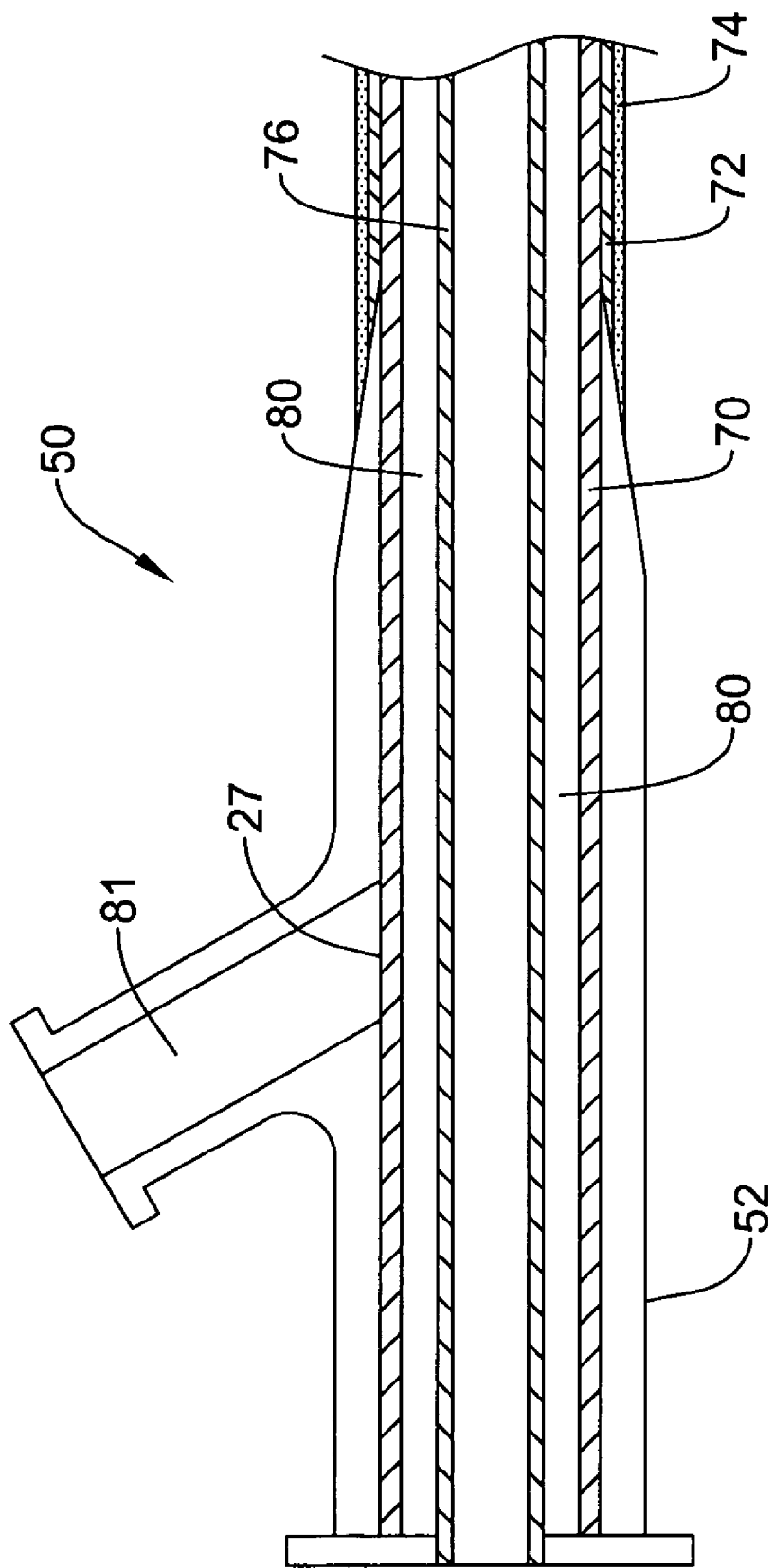
FIG. 9 is a cross-sectional view of the proximal portion of a catheter in accordance with an embodiment of the invention.

FIG. 9 shows one embodiment of the proximal portion 30 of the catheter 10. Proximal portion 30 includes a hub assembly 50. Hub assembly 50 includes hub 52 disposed about a portion of elongate shaft 15. Outer tubular member 70 extends into at least a portion of hub 50. Inner tubular member 76 may extend into at least a portion of hub 50 and may provide a working lumen 78 extending to the proximal end of hub 52 for use during a medical procedure. As shown in FIG. 9, polymer layer 72 may terminate distal of the hub assembly 50. Termination of polymer layer 72 distal of hub assembly 50 provides a proximal segment 27 of outer tubular member 70 free of the polymer layer 72. Proximal segment 27 may include a plurality of apertures 100 disposed along outer tubular member 70 unobstructed by the polymer layer 72. Unobstructed apertures 100 may be a subset of the apertures 100 extending along the length of the outer tubular member 70. Unobstructed apertures 100 along proximal segment 27 are preferably formed during the same process as forming apertures 100 along the length of the outer tubular member 70, as discussed above. At least some of apertures 100 disposed along proximal segment 27 extend through the wall of outer tubular member 70. The hub assembly 50 may also include an inflation port 81. Inflation port 81 may be disposed about at least a portion of the elongate shaft 15 including the proximal segment 27 having unobstructed apertures 100. Unobstructed apertures 100 in proximal segment 27 provide fluid communication between inflation port 81 and inflation lumen 80 of catheter 10.

Figure 10:
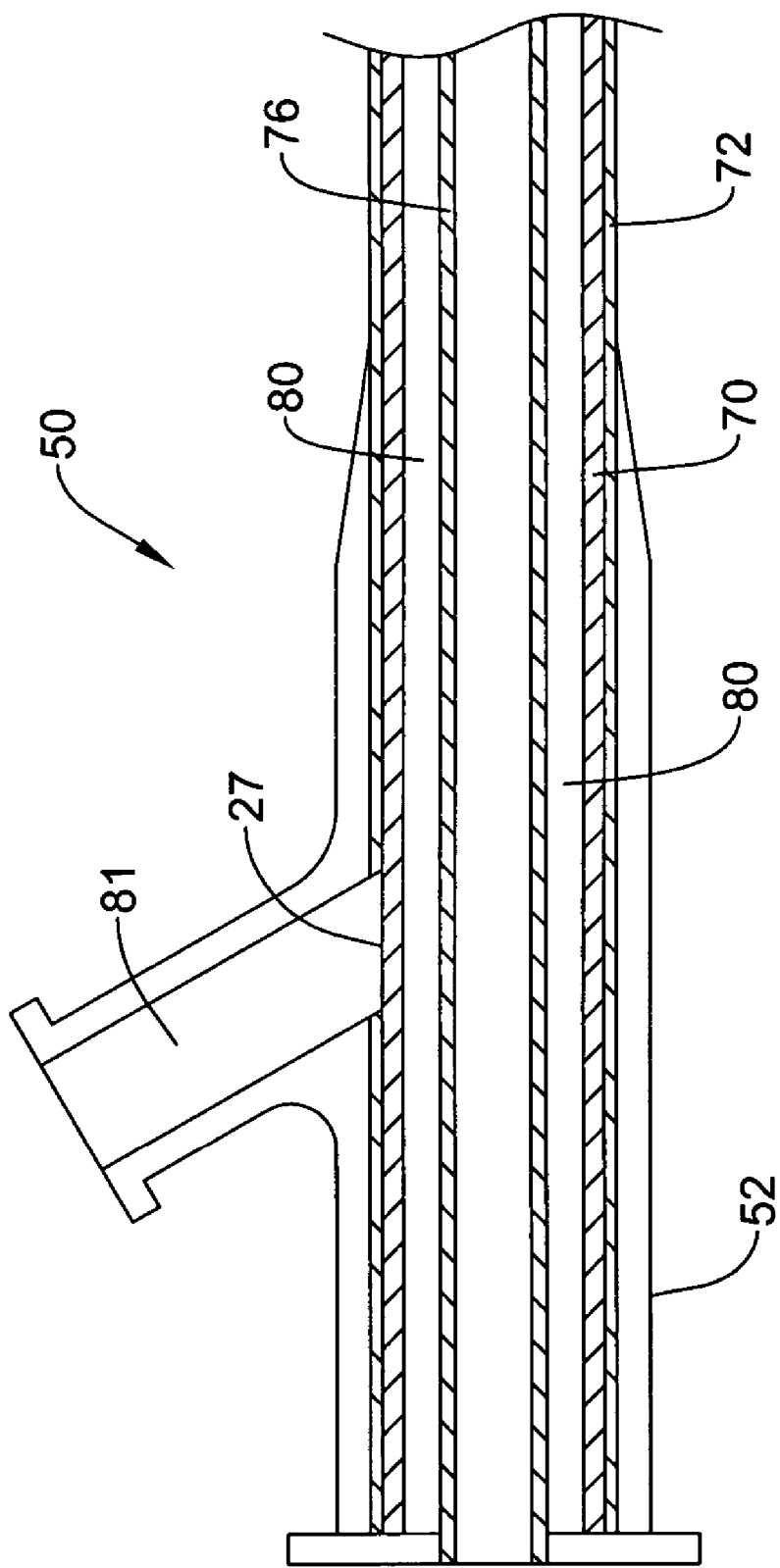
FIG. 10 is a cross-sectional view of the proximal portion of another catheter in accordance with an embodiment of the invention and FIG. 11 is a cross-sectional view of the proximal portion of another catheter in accordance with an embodiment of the invention.

FIG. 10 shows another embodiment of the proximal portion 30 of the catheter 10 in accordance with the invention. In this embodiment, polymer layer 72 extends into at least a portion of the hub assembly. However, proximal segment 27 adjacent to inflation port 81 is free of the polymer layer 72, such that a plurality of apertures 100 are unobstructed by the polymer layer 72 along proximal segment 27.

Figure 11:
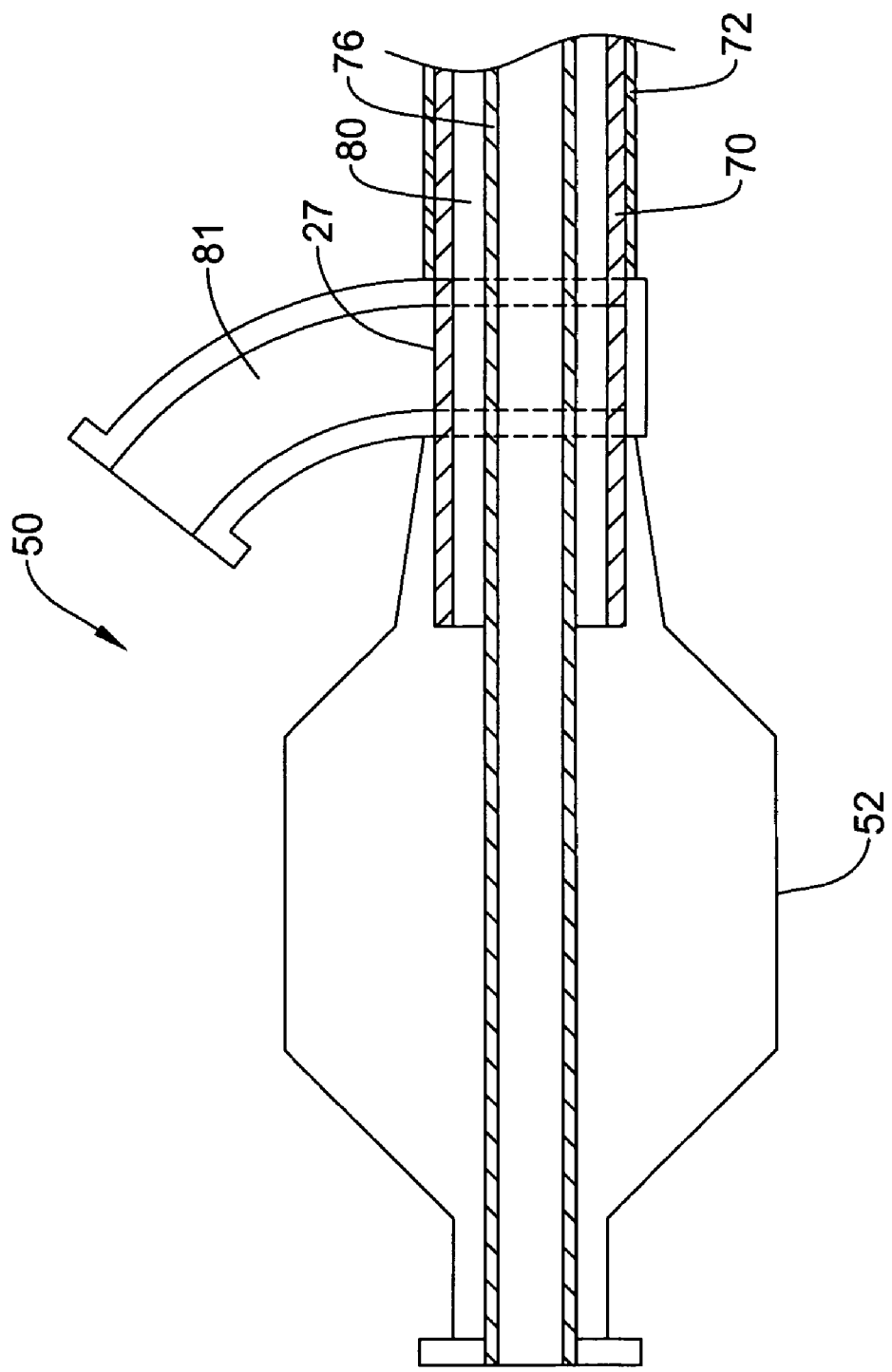

FIG. 11 shows another embodiment of the proximal portion 30 of the catheter 10 in accordance with the invention. Hub assembly 50 may include a hub 52 and an inflation port 81. Inflation port 81 is disposed about at least a portion of proximal segment 27 free of the polymer layer 72. Unobstructed apertures 100 provide fluid communication between inflation port 81 and inflation lumen 80. Inner tubular member 76 may extend substantially to distal end of the hub 50 to provide a working lumen 78.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What we claim is:

1. A medical device comprising:
   an elongate shaft including a metallic tube having a proximal end, a distal end, a length and a lumen extending therethrough, the metallic tube having an outer surface and an inner surface defining a wall therebetween, wherein the metallic tube includes a plurality of apertures extending through the wall along at least a portion of the length to facilitate bending;
   a polymer layer disposed about at least a portion of the metallic tube, wherein at least a portion of the plurality of apertures are fluidly sealed, a distal portion of the metallic tube having a subset of the plurality of apertures being free of the polymer coating; and
   an inflatable balloon disposed about at least the distal portion of the metallic tube having a plurality of the apertures free of the polymer coating; wherein the inflatable balloon is in fluid communication with the lumen of the metallic tube.

2. The medical device of claim 1, further comprising:
   an inner tubular member disposed in at least a portion of the metallic tube, the inner tubular member having an outer surface spaced away from the inner surface of the metallic tube, defining an annular inflation lumen therebetween in fluid communication with the inflatable balloon.

3. The medical device of claim 2, further comprising:
   a proximal portion of the metallic tube having a subset of the plurality of apertures being free of the polymer layer; and
   a hub assembly having an inflation port disposed about at least the proximal portion of the metallic tube having a subset of the plurality of apertures being free of the polymer layer, wherein the inflation port is in fluid communication with the annular inflation lumen.

4. The medical device of claim 1, further comprising:
   a proximal portion of the metallic tube having a subset of the plurality of apertures being free of the polymer layer; and
   a hub assembly having an inflation port disposed about at least the proximal portion of the metallic tube having a subset of the plurality of apertures being free of the polymer layer, wherein the inflation port is in fluid communication with the inflatable balloon.

5. The medical device of claim 1, wherein the plurality of apertures are micromachined.

6. The medical device of claim 1, wherein the plurality of apertures extend substantially the length of the metallic tube.

7. The medical device of claim 2, further comprising a distal tip.

8. The medical device of claim 7, wherein the inner tubular member extends distal of the distal end of the metallic tube, wherein the distal tip includes the inner tubular member.

9. The medical device of claim 7, wherein the distal tip includes a coil.

10. The medical device of claim 7, wherein the distal tip occludes the lumen of the metallic tube at the distal end.

11. The medical device of claim 1, wherein the metallic tube is a nickel-titanium alloy.

12. The medical device of claim 1, wherein the metallic tube is a stainless steel.

13. The medical device of claim 1, wherein the polymer layer is PEBAX.

14. The medical device of claim 1, further comprising a hydrophilic coating disposed over at least a portion of the polymer layer.

15. A medical device comprising:
   an elongate shaft having a proximal end, a distal end, a length and a lumen extending therethrough, the elongate shaft including a plurality of micromachined apertures along at least a portion of the length to facilitate bending;
   a polymer layer disposed on at least a portion of the elongate shaft, the polymer layer fluidly sealing at least a portion of the plurality of micromachined apertures, a distal portion of the elongate shaft including at least one of the plurality of micromachined apertures being free of the polymer layer;
   an inner tubular member disposed in the lumen of the elongate shaft, the inner tubular member having an outer surface and the elongate shaft having an inner surface;
   an inflation lumen defined by a space between the outer surface of the inner tubular member and the inner surface of the elongate shaft;
   an inflatable balloon disposed about at least the distal portion of the elongate shaft being free of the polymer layer, the inflatable balloon in fluid communication with the inflation lumen.

16. The medical device of claim 15, further comprising:
   a proximal portion of the elongate shaft including at least one of the plurality of micromachined apertures being free of the polymer layer; and
   a hub assembly having an inflation port disposed about at least the proximal portion of the elongate shaft being free of the polymer layer, wherein the inflation port is in fluid communication with the inflatable balloon.

17. The medical device of claim 15, wherein the micromachined apertures extend substantially the length of the elongate shaft.

18. The medical device of claim 15, further comprising a distal tip.

19. The medical device of claim 18, wherein the distal tip includes a coil.

20. The medical device of claim 18, wherein the distal tip occludes the inflation lumen at the distal end of the elongate shaft.

21. The medical device of claim 15, wherein the elongate shaft is a nickel-titanium alloy.

22. The medical device of claim 15, wherein the elongate shaft is a stainless steel.

23. The medical device of claim 15, wherein the polymer layer is PEBAX.

24. The medical device of claim 15, further comprising a hydrophilic coating disposed over at least a portion of the polymer layer.

25. A medical device comprising:
   an elongate shaft including a metallic tube having a proximal end, a distal end and a lumen extending therethrough, the metallic tube having an inner surface and an outer surface defining a wall therebetween, wherein the metallic tube includes a plurality of micromachined apertures to facilitate bending extending through the wall of at least a portion of a proximal section, an intermediate section, and a distal section of the tubular member, a polymer layer disposed about at least the intermediate section of the metallic tube, wherein a subset of the plurality of micromachined apertures are fluidly sealed, the proximal section and the distal section being free of the polymer layer, an inner tubular member disposed in the lumen of the metallic tube, the inner tubular member having an outer surface, an annular inflation lumen defined by a space between the outer surface of the inner tubular member and the inner surface of the metallic tube, a hub assembly including an inflation port disposed about at least the proximal section of the metallic tube, an inflatable balloon disposed about at least the distal section of the metallic tube, and an inflation passageway defined by the inflation port, the plurality of micromachined apertures of the proximal section of the metallic tube, the annular inflation lumen, the plurality of micromachined apertures of the distal section of the metallic tube, and the inflatable balloon.

26. The medical device of claim 25, wherein the metallic tube is a nickel-titanium alloy.

27. The medical device of claim 25, wherein the metallic tube is a stainless steel.

28. The medical device of claim 25, wherein the polymer layer is PEBAX.

29. The medical device of claim 25, further comprising a hydrophilic coating disposed over at least a portion of the polymer layer.

* * * * *

UNITED STATES PATENT AND TRADEMARK OFFICE
CERTIFICATE OF CORRECTION

PATENT NO. : 7,632,242 B2  Page 1 of 1
APPLICATION NO. : 11/008452
DATED : December 15, 2009
INVENTOR(S) : Griffin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1190 days.

Signed and Sealed this

Second Day of November, 2010

David J. Kappos
*Director of the United States Patent and Trademark Office*